United States Patent [19]

Ollivier et al.

[11] 4,233,128
[45] Nov. 11, 1980

[54] PHOTOSYNTHESIS OF MERCAPTANS

[75] Inventors: Jean Ollivier, Arudy; Guy Souloumiac; Jeannine Suberlucq, both of Pau, France

[73] Assignee: Societe Nationale Elf-Aquitaine (Production), Paris, France

[21] Appl. No.: 34,616

[22] Filed: Apr. 30, 1979

[30] Foreign Application Priority Data

May 5, 1978 [FR] France .................................. 78 13341

[51] Int. Cl.$^3$ ............................................. B01J 19/08
[52] U.S. Cl. ............................ 204/158 R; 204/162 R
[58] Field of Search ....................... 204/158 R, 162 R

[56] References Cited

U.S. PATENT DOCUMENTS

| | | | |
|---|---|---|---|
| 3,567,608 | 3/1971 | Warner | 204/158 N |
| 4,052,283 | 10/1977 | Dannels | 204/158 N |

*Primary Examiner*—Howard S. Williams
*Attorney, Agent, or Firm*—Ostrolenk, Faber, Gerb & Soffen

[57] ABSTRACT

Synthesis of mercaptans by the photochemical reaction of an olefin with hydrogen sulphide in the presence of an initiator constituted by benzophenone, thiobenzophenone or a mixture of the two, preferably accompanied by an organic compound of an element of Group VA of the Periodic Classification. These initiators can carry substituents on either or both of the two benzene rings. The light utilized can have a wavelength of 300 to 600 nm. The process allows various mercaptans to be obtained with good yields.

12 Claims, No Drawings

PHOTOSYNTHESIS OF MERCAPTANS

BACKGROUND OF THE INVENTION

The present invention comprises an improvement in the production of mercaptans starting from ethylenic compounds, by reaction of the latter with hydrogen sulphide. It relates, in particular, to the photochemical synthesis of mercaptans from olefins and from ethylenic esters in the liquid phase.

In view of the well-known industrial utility of various mercaptans, methods of preparation of these substances have given rise to numerous studies. One process which has led to interesting industrial results is based on the direct action of hydrogen sulphide on ethylenic substances, under the effect of ultraviolet radiation. In carrying out this process, the technique is to introduce into the reaction medium promoter agents, in particular, organic phosphites, as described, for example, in U.S. Pat. No. 3,050,452. The photochemical creation of SH radicals, which should be induced by the addition to $H_2S$ to the double bond of the ethylenic compound, implies the utilization of ultraviolet radiation of short wavelength, which causes certain disadvantages. In practice, it is necessary to utilize agents and solvents which are particularly pure and transparent. On the other hand, the optical transmission in the reactor is poor because of the high coefficient of molecular extinction of hydrogen sulphide. In addition, the synthesised mercaptan itself absorbs radiation and this causes a considerable deceleration of the reactions for only slightly elevated degrees of progress, with the formation of sulphides by the addition of the mercaptan itself to the double bond of the ethylenic compound.

In order to avoid these disadvantages and carry out industrially the above-indicated process with suitable reaction speeds and yields, it is thus necessary to be able to effect the photochemical addition over a larger wavelength range, namely approaching the visible spectrum or even with visible light.

SUMMARY OF THE INVENTION

The present invention provides an exact solution to this problem, by the use of a sensitising substance which can be excited in a wavelength range above 300 nm, even though the sole industrial results obtained up to the present required wavelengths below 300 nm.

The process according to the invention is characterised in that the usual reaction medium, containing a promoter comprising an organic derivative of an element of Group VA of the Periodic Classification of the elements, also includes benzophenone and/or thiobenzophenone or even one or more derivatives of these aryl ketones.

The additives according to the invention allow the photochemical synthesis of mercaptans to be effected in a wavelength range extending from about 300 nm to 600 nm. In fact, the addition of benzophenone, $C_6H_5COC_6H_5$, the absorption spectrum of the first reactive excited state of which covers the range from 300 to 400 nm, thus allows operation with ultraviolet very close to the visible spectrum. Thiobenzophenone, $C_6H_5CSC_6H_5$, is active in the range from 350 to 600 nm which, as can be seen, overlaps the visible range, as the latter extends from 400 to 750 nm. The simultaneous use of benzophenone and thiobenzophenone in appropriate proportions gives the advantage of allowing operation over the very large wavelength range of 300 to 600 nm. It is thus possible to obtain the maximum benefit from the energy emitted by the most powerful ultraviolet generators which are at present available on the industrial market.

While non-substituted benzophenone and thiobenzophenone give excellent results, it can also be useful to employ certain of their derivatives, particularly compounds in which one or both of the benzene rings carry substituents such as alkyl groups, halogens, hydroxyl, carboxyl or alkoxy groups or esters.

The promoters of the known art which are mostly used are the trialkyl and triaryl phosphites. The ketones and thiones according to the present invention give good results in conjuction with them, but these derivatives of phosphorus can be replaced or accompanied by organic derivatives of Bi, As, or Sb.

The additives according to the invention amplify the initiator effect of known agents, particularly the phosphites mentioned above, and limit the inhibitive action of the sulphides, ultimately formed by a secondary reaction, produced on formation of the desired mercaptan.

While ketones and aryl thiones according to the invention can be utilized alone as photochemical initiators in the wavelength range above 300 nm, they give remarkably better results than the known promoters when they are employed in conjunction with organic compounds of elements of Group VA of the Periodic Classification, in particular triaryl and trialkyl phosphites.

For example, in the synthesis of n-propanethiol starting from propylene and $H_2S$, in the presence of 350 nm ultraviolet, with 0.06 mole of tridecyl phosphite per liter of reaction medium, slightly less than half the quantity of n-propanethiol is obtained than is given by 0.014 mole of benzophenone. However, if the same proportions of these two initiators are used at the same time, the quantity of mercaptan obtained is about 2.58 times larger than that given by tridecyl phosphite alone. It can thus be seen that the benzophenones and thiobenzophenones provide a very marked advantage over the older initiators. These results are all the more unexpected in that a ketone, particularly acetone, has been proposed as a promoter for a photochemical reaction of certain mercaptans with polybutadiene (U.S. Pat. No. 3,338,810). The present invention shows that, in contrast to acetone, benzophenones and thiobenzophenones do not have chemical reactivity vis-a-vis the hydrogen sulphide or the mercaptan formed.

The proportions of initiators according to the invention to be added to the reaction medium depend on various factors, particularly the nature of the reactants treated, their concentration in the medium, the presence or absence of solvent and so on. Most often, the proportions are of the order of 0.001 to 0.05 mole per liter of reaction medium, preferably 0.0015 to 0.0075.

The process of the invention is preferably carried out in a solvent, which can be, for example, a hydrocarbon or an ether, but not a sulphide. Solvents which are particularly suitable include methylal, glyoxal, the dimethyl ether of ethylene glycol, the dimethyl ether of diethylene glycol, benzene, toluene, hexane, decane and dodecane, methylal being a particularly preferred solvent.

As regards the operative conditions, in particular the temperatures and the $H_2S$/olefin proportions, they are the same as in the corresponding technique already known from prior publications. There is thus no need for them to be described in detail here. It will be noted only that the preferred H₂S/olefin molar ratios are around 3 to 10, the temperature being maintained at 0° to 20° C.; temperatures ranging from −5° to +35° nevertheless being utilizable, though being somewhat less advantageous.

As regards the nature of the ethylenic compounds, transformation of which into mercaptans can be improved by the process of the invention, reference can be made, by way of example, to ethylene, propylene, butene-1, butene-2, isobutene, pentene-1, pentene-2, hexene-1, heptene-1, octene-1, decene-1, undecene-1, dodecene-1, tetradecene-1, hexadecene-1, octadecene-1, eicosene-1, isopentene-1, 4-methyl-pentene-1, 3,6-dimethyl-heptene-1, 4-methyl-5-butyl-decene-4, 1,4-diphenyl-butene-2, 3-cyclohexyl-eicosene-6, 4-methyl-pentene-2, 2,4,4-trimethyl-pentene-2-cyclopentene, 2,5-diethyl-cyclopentene, cyclohexene, 3-ethyl-cyclohexene, cyclopentene, cyclooctene, 4-vinyl-cyclohexene, alkyl esters of acrylic, methacrylic, crotonic, allylacetic (pentenoic), octylenic, undecylenic, dodecylenic, octadecylenic and other acids etc; the esters in question can in particular contain alkyl groups from $C_1$ to $C_{30}$ and more particularly from $C_1$ to $C_8$. The ethylenic compounds can have several double bonds, as is the case, for example, with butadiene and hexadiene-2,4.

The non-limitative examples which follow illustrate the invention.

COMPARATIVE EXAMPLES 1 TO 3

The following preparations have been effected according to a mode of operation known per se.

The "Pyrex" photochemical reactor was of the standard type, having a submerged coaxial lamp and a fritted glass base to obtain good diffusion of the hydrogen sulphide and propylene gases. The volume irradiated was 130 ml. The reactor was thermostated by a double exterior envelope and was operated discontinuously at ambient pressure, the gas input rates being maintained constant throughout the experiment. These are, in particular, 30 l/hour for H₂S and 28 l/hour for propylene. The solvent was the dimethyl ether of diethylene glycol and the temperature, at which it was saturated with hydrogen sulphide and propylene, was 0° C. The photosensitized concentration corresponds as a rule to the optimum profile of the intensity absorbed in the reactor. The luminous source was a low-pressure mercury lamp with average reemission at around 350 nm. Its power was 8 watts. After 35 minutes, the quantities of mercaptan formed were:

| Example | Initiator | Mole of Mercaptan |
| --- | --- | --- |
| 1 | Benzophenone alone-0.014 mole/liter | 0.12 |
| 2 | Tridecyl phosphite-0.060 mole/liter | 0.07 |
| 3 | Benzophenone-0.014 mole/liter-in conjunction with tridecyl phosphite-0.060 mole/liter | 0.18 |

Example 3 shows that the conjoint use of benzophenone and the phosphite gives a quantity of mercaptan which is 2.58 times larger than that provided by the phosphite alone.

EXAMPLE 4

Preparation of n-propyl-thiol

The photochemical reaction was carried out in a cylindrical 250 ml "Pyrex" reactor with a submerged coaxial lamp. Refrigeration and agitation of the reaction medium were provided by an exterior coil cooled so as to maintain the temperature at around 18° C. The reactor was equipped with an 8 watt fluorescent lamp, averaged around 350 nm.

160 ml of the dimethyl ether of diethylene glycol (diglyme) was introduced into the reactor. This solvent was then saturated under a pressure of 3 bars with a gaseous mixture of H₂S and propylene. The input of hydrogen sulphide was 90 l/hour and that of propylene 30 l/hour and these input rates were maintained throughout the duration of the operation.

A pulse absorber at the gas outlet to the burn-off torch allowed a constant pressure to be maintained within the reactor. The system was connected to a safety valve under a nitrogen counter-pressure. An electro-valve located at the level of the reactants allowed regular evacuation of the effluent, which was recovered after passing through a depressurization chamber forming a gas lock.

The solvent contained per liter 0.0055 mole of benzophenone and 0.0022 mole of triphenyl phosphite. It was adjusted continuously by means of a metering pump at the rate of 350 ml/l.

When a continuous stable regime was attained in the reactor, the volume of the reaction mixture was 240 ml.

Thus, the reactor produced continuously per hour 20.13 g of n-propylthiol and 4.04 g of dipropyl sulphide. The mass yield of mercaptan was thus 83.3%. The mercaptan was recovered by distillation after sparging off the residual H₂S and propylene, which were recycled.

EXAMPLE 5

The operations of Example 4 were repeated by injecting 120 liters per hour of hydrogen sulphide and 10 liters per hour of propylene. The production was 21.5 g per hour with a 90% yield of mercaptan.

EXAMPLE 6

The operations of Example 1 were repeated with butene-1 in place of propylene. 0.280 mole of butyl mercaptan were thus obtained.

EXAMPLE 7

Using the operative mode of Example 1, the benzophenone was replaced with thiobenzophenone $(5,10^{-4}MC^{-1})$, all the other conditions being unchanged. The quantity of mercaptan formed was 0.150 M.

EXAMPLE 8

In the operations of Example 1, the dimethyl ether of diethylene glycol was replaced by a solvent constituted by dodecane. The yield of mercaptan was 24% for 0.172 mole of mercaptan+sulphide formed.

EXAMPLE 9

Under the operations of Example 1, the dimethyl ether was replaced by methylal. The quantity of mercaptan formed was 0.268 mole.

EXAMPLE 10

Under the conditions of Example 3, hydrogen sulphide was injected into the reaction medium at a rate of 38 liters per hour. Thereafter, irradiation was effected on 153 mmoles of octene-1 dissolved in diglyme in an amount of 1.274 mole per liter, containing the same radical photo-initiators as in Example 3. The temperature was 1° C. After 5 minutes, 81 mmoles of n-octyl mercaptan were formed.

EXAMPLE 11

Under the conditions of Example 3, with an input of 38 liters per hour of hydrogen sulphide, 67.7 mmoles of dodecene-1 dissolved in diglyme at a concentration of 0.564 mole per liter were irradiated at 11° C. After 3 minutes of irradiation, 48.2 mmoles of n-dodecyl mercaptan were formed.

EXAMPLE 12

Preparation of methyl 11-mercapto-undecanoate

In the apparatus of Example 4, a solution of 200 ml of methyl undecylenate in 660 ml of diglyme was injected, containing per liter 2 g of benzophenone and 1.8 g of triphenyl phosphite. This injection was effected continuously under a pressure of 5 bars, at the rate of 200 ml per hour. The input of $H_2S$ which traversed the reaction medium ws 120 l/h. The operation took place at 15° C. From the effluent, 94 g of methyl mercapto-undecanoate and 3 g of the corresponding symmetrical sulphide were extracted. The mercaptan selectivity was about 97%.

We claim:

1. In the method of synthesizing a mercaptan by the photochemical reaction between an ethylenically unsaturated compound and hydrogen sulfide, in the presence of a group VA element promoter, the improvement which comprises the reaction medium containing a ketone selected from the group consisting of benzophenone, thiobenzophenone and substituted benzophenones and thiobenzophenones.

2. Method according to claim 1, wherein said substituents are alkyls, hydroxyls, halogens, carboxyls, alkoxies or ethers.

3. Method according to claim 1, wherein the light used in the photochemical reaction has a wave length in the range of 300 to 400 nm, and the ketone is benzophenone.

4. The method according to claim 1, wherein the light used in the photochemical reaction has a wave length of 350 to 600 nm, and the ketone is thiobenzophenone.

5. The method according to claim 1, wherein the light used in the photochemical reaction comprises several wave lengths of 300 to 600 nm and the ketone is a mixture of benzophenone and thiobenzophenone.

6. The method according to claim 1, wherein the reaction medium contains 0.001 to 0.05 mole ketone per liter.

7. The method according to claim 6, wherein the amount of ketone is 0.0015 to 0.0075 mole per liter.

8. The method according to claim 1, wherein the photochemical reaction is effected a solvent constituted by an ethylene glycol ether, within a hydrocarbon or methylal.

9. The method according to claim 6, wherein the molar ratio of said compound to said hydrogen sulfide is about 3–10 and the temperature is −5° to 35° C.

10. The method according to claim 9, wherein the temperature is 0°–20° C. and the amount of ketone is 0.0015 to 0.0075 mole per liter.

11. The method of claim 10, wherein said promoter is an organic phosphite.

12. The method of claim 10, wherein said promoter is a tridecyl phosphite.

* * * * *